United States Patent [19]

Buro et al.

[11] Patent Number: 4,935,726

[45] Date of Patent: Jun. 19, 1990

[54] DRAINAGE SYSTEM MONITORING APPARATUS

[75] Inventors: Timothy Buro, Fullerton; Donald L. Hollenbeck, Brea; Robert A. Rauch, Santa Ana, all of Calif.

[73] Assignee: Underground Sensor Systems, Inc., Brea, Calif.

[21] Appl. No.: 283,578

[22] Filed: Dec. 14, 1988

[51] Int. Cl.$^5$ .............................................. G08B 21/00
[52] U.S. Cl. .................................... 340/603; 73/61.1 R
[58] Field of Search .......... 340/603; 73/61 R, 61.1 R, 73/53

[56] References Cited

U.S. PATENT DOCUMENTS

| | | | |
|---|---|---|---|
| 3,214,964 | 11/1965 | Davis | 73/61 R X |
| 3,762,214 | 10/1973 | Bogusz | 73/61 R |
| 3,839,902 | 10/1974 | Scott et al. | 73/61 R |
| 4,549,171 | 10/1985 | Akiba et al. | 73/61 R X |

FOREIGN PATENT DOCUMENTS 1020467 12/1957 Fed. Rep. of Germany ... 73/61.1 R
7601382 2/1976 Netherlands ..................... 73/61.1 R

OTHER PUBLICATIONS

Bock, D. H. et al., *Detection of Oil in Sewers.* In IEEE Transact. on Geoscience Electronics vol. GE-10, No. 2 Apr. 1972, pp. 119-126.

*Primary Examiner*—Hezron E. Williams
*Assistant Examiner*—Joseph W. Roskos
*Attorney, Agent, or Firm*—G. Donald Weber, Jr.

[57] ABSTRACT

This invention is directed to an apparatus or system which is used for monitoring a storm drain system in order to detect the presence of hydrocarbons or the like therein. The apparatus includes a sensor unit which is arranged to float on the surface of the storm drain effluent. A suitable alarm system is connected to the sensor unit to indicate an activation of the sensor unit. The storm drain is, typically, modified to provide a uniform sensing area adjacent to the sensor unit.

27 Claims, 2 Drawing Sheets

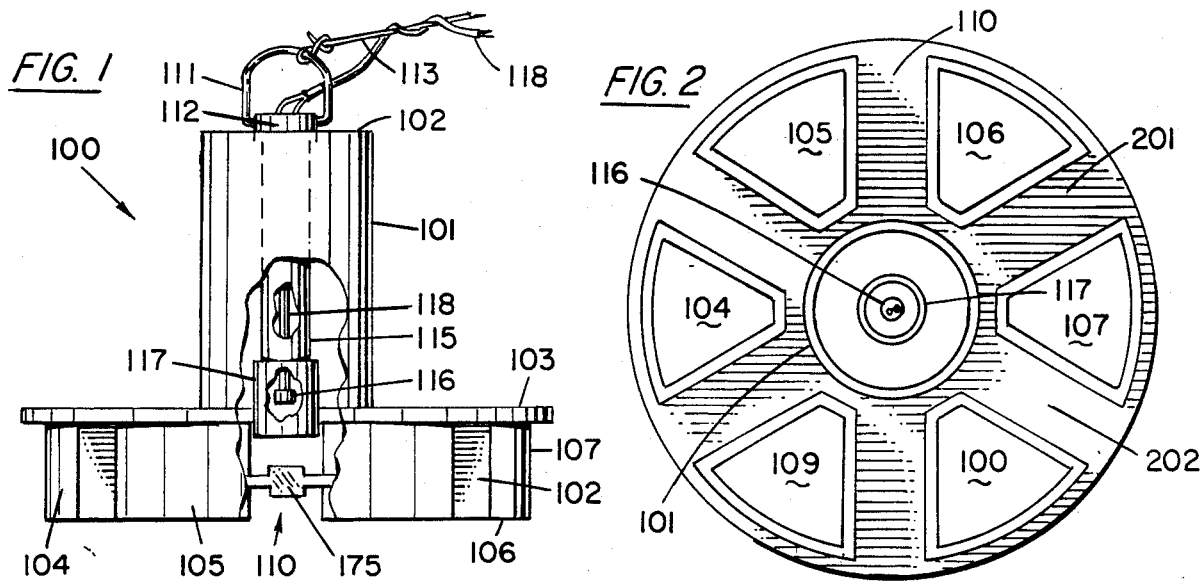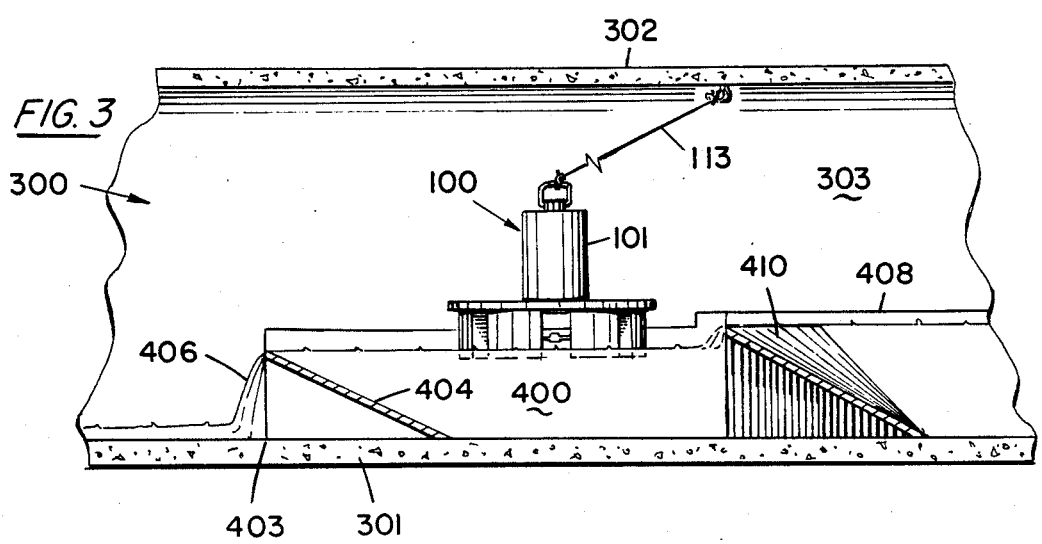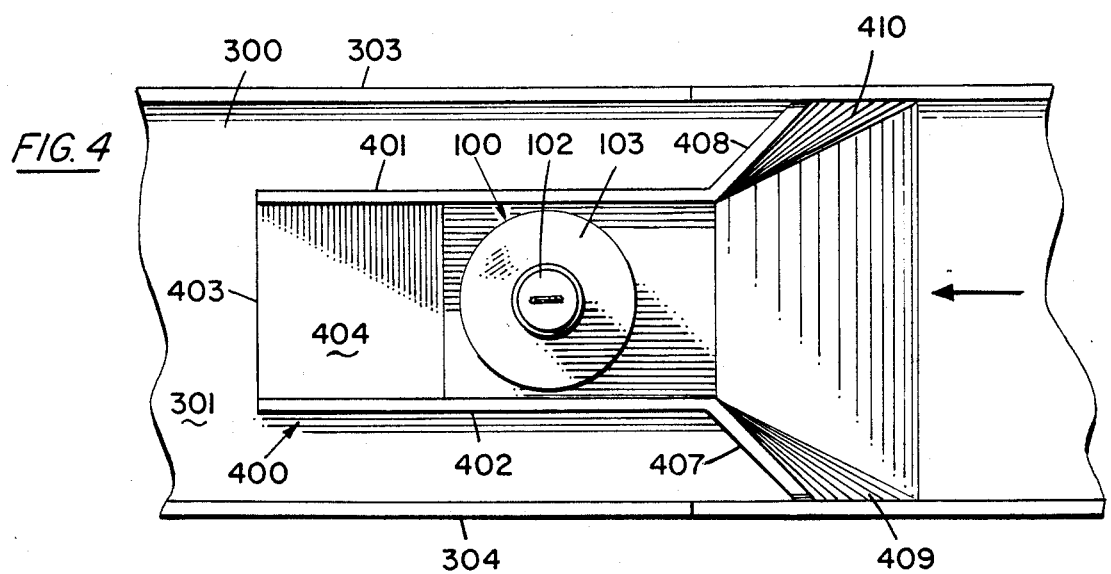

DRAINAGE SYSTEM MONITORING APPARATUS

BACKGROUND

1. Field of the Invention.

This invention directed to a sensing system, in general, and, in particular, to a sensing or detecting system which is used to detect toxic, hazardous or otherwise undesirable materials in a drainage system and to provide a suitable alarm signal when such materials are detected.

2. Prior Art.

One of the most visible problems of health and waste management techniques in this day and age is the impact of hazardous and/or toxic wastes and the disposal thereof. This disposal can be in accordance with accepted legal practices or not. Generally, legal disposal is monitored and kept within relatively safe parameters. Other disposals are not performed under controlled conditions. These uncontrolled disposals can be in the nature of overt or deliberate disposal such as dumping or the like. Conversely, uncontrolled disposals can be inadvertent disposals problems such as occur during involuntary spills, leakages, overflows or the like.

One of the areas of concern is the incursion of such wastes into drainage systems, whether deliberate or unintentional. This is especially a problem in those areas where the drainage system is permitted to empty, untreated into an adjacent body of water such as a lake, ocean, river, or the like. However, as environmentalists (among others) have determined, the continual dumping (deliberate or unintentional) of such wastes into such bodies of water is undesirable. These bodies of water become contaminated, the marine life suffers, tide pools are affected and the entire ecological system is eroded. Consequently, it is highly desirable to determine if and when certain wastes are found in the effluent being discharged by a drainage system.

It is equally desirable to determine when such wastes have accumulated to a substantial degree in storm drain systems. This can occur due to leakage, dumping, or merely as a result of certain wastes entering the drainage systems from streets during light rains, street cleaning, and so forth. That is, the wastes are washed from the surface streets into storm sewers and onward to the discharge location. While not necessarily so insidious, these wastes are just as damaging to the environment.

In a related environmental protection operation, a detection scheme is used in conjunction with detection of leaks from undergound tanks or the like. In this scheme, a hole is drilled into the ground adjacent to the underground tank, a vadous zone is created by inserting a suitable well liner, for example PVC pipe, into the hole, and a hydrocarbon detector is inserted therein. This detector can include a sensor probe which detects hydrocarbon, water and other elements.

In this system, if a leak occurs at the underground tank, the waste material seeps into the vadous zone and is detected by the sensor. However, this situation includes and comprises a known trouble spot (i.e. a buried tank) in a substantially fixed location wherein the vadous zone is relatively simple to produce.

In order to monitor drainage systems such as storm drains or the like, the water flow, the water depth, the drainage system and other variables must be considered while attempting to obtain a reliable, repeatable, detection operation. Consequently, the system of the instant invention is provided.

SUMMARY OF THE INSTANT INVENTION

This invention is directed to a monitoring system especially useful for drainage systems. In particular, it is used to detect certain undesirable contaminants in the water (or other effluent) which is usually handled by the drainage system.

An appropriate sensor element is mounted in a sensor element container to provide a sensor unit. In a preferred embodiment, this container is capable of floating on water and most other liquids. The container includes a chamber in which the sensor element is mounted and in which appropriate fluids, liqids, gases, fumes, and the like can accumulate in the presence of the sensor element. The sensor element (and the container) are tethered within the drainage system and connected to suitable alarm systems for indicating the presence of the undesirable wastes in the effluent.

The drainage system, or channel, can be modified to ensure that the water flow or effluent flow through the drainage channel is contained within a preferred area, or volume, adjacent to the sensor element container (and, thus, the sensor element) in order to assure optimum operation of the monitoring system.

In a preferred embodiment, the alarm system can indicate the presence of a spill in a particular location in the drainage system. In other embodiments, tha alarm system can, under prescribed conditions, cause a gate or other mechanism to close the drainage system until the hazardous effluent can be removed whereby the hazardous material is not discharged into the environment.

BRIEF DESCRIPTION OF THE DRAWINGS.

FIG. 1 is a partially broken away, side view of the sensor unit comprising the sensor element container and sensor element of the instant invention.

FIG. 2 is a bottom view of the sensor element container as shown in FIG. 1.

FIG. 3 is a schematic side view of a drainage channel section using a sensor unit of the instant invention.

FIG. 4 is a top or plan view of a portion of the drainage channel section shown schematically in FIG. 3.

DESCRIPTION OF THE PREFERRED EMBODIMENTS

Figure 5:
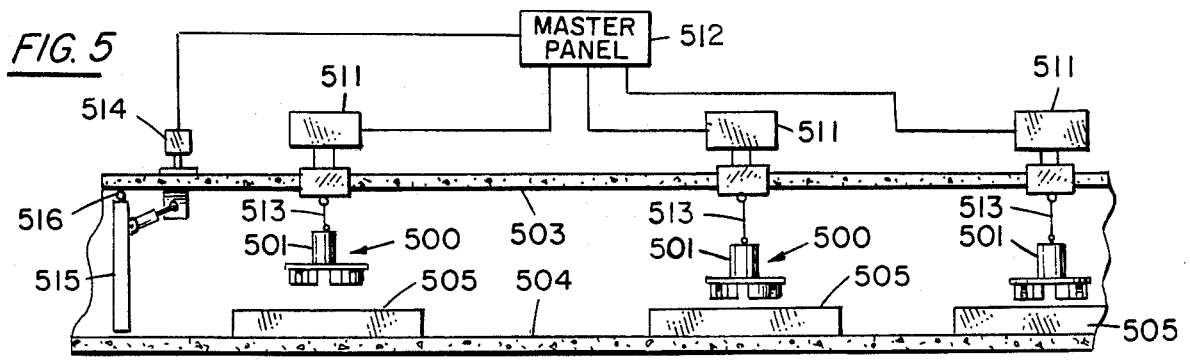
FIG. 5 is a schematic representation of a drainage system comprising multiple sensor units disposed along the length of the drainage system.

Referring now to FIG. 1, there is shown a partially broken away, schematic representation of one embodiment of the sensor element and sensor element container (hereinafter the sensor float) on the instant invention. The sensor float 100 comprises a housing fabricated, typically, of a lightweight but strong and durable plastic such as polyvinyl chloride (PVC). The sensor float 100 includes an upper housing 101 which is essentially cup-shaped. In the preferred embodiment, the upper housing 101 is cylindrical in shape and may be formed from a piece of PVC pipe of the appropriate internal diameter. The upper end of housing 101 is closed by a cap 102 which is attached to (or formed as) part of the upper housing 101. The bottom end of housing 101 remains open. However, the bottom edge of housing 101 is joined to a wafer or disk shaped member 103 which is formed of the same material as the remainder of float 100.

Typically, the disk 103 is joined to the open end of housing 101 by means of appropriate adhesive, welding or any other suitable technique. On the under surface of disk 103 are formed a plurality of compartments 104, 105, 106 and 107. These compartments are, typically, wedged shaped. The respective compartments can be formed of a plurality of walls which are joined together and fastened to disk 103. Conversely, each compartment can be built with a lightweight material such as Kapok or the like. In either event, the compartment is arranged to provide a bouyancy for the float element 100. With this construction, the float element 100 will, in fact, float on the surface of the water or other material in the drainage system. Of course, the depth to which the float 100 sinks or floats upon the liquid surface is variable. However, it is typically arranged so that the water surface extends approximately half way up the height of the respective compartments.

Thus, the water will pass through the channel 110 (and other similar channels) between the compartments. However, the float or bouyancy factor of the float mechanism 100 is such that as the water passes through the channel 100, it will not encounter the sensor element 116 in the sensor float.

Also attached to the cap 102 of the sensor float 100 is a suitable connector 111. As shown in the instant embodiment, the connector 111 is a ring which is attached to the cap 102 by means of a suitable fastening arrangement such as a threaded connector or the like. A tethering apparatus 113 is connected to the connector ring 111. In a typical case, the tethering apparatus 113 is in the form of a support wire or the like. More particularly, in a preferred embodiment the support wire is fabricated of stainless steel or the like which provides suitable strength, rust resistance and so forth.

A suitable length of pipe 115 is also mounted within housing 101. The pipe 115 is, typically, arranged to connect to the connector ring 111 through the threaded connector 112. The pipe 115 is, typically, a tube formed of a suitable material such as stainless steel, or the like which is sufficiently strong to remain rigid, retain the sensor element 116 described hereinafter and be resistant to corrosion in the environment of the sensing system.

A suitable sensor 116 is shown schematically. The sensor 116 is of the type of device as referred to as an Adsistor detection device. (Adsistor is registered trademark of a Adsistor Technology, Inc.). This type of detector or sensor is capable of detecting, inter alia, hydrocarbon materials and is described, for example, in U.S. Pat. Nos. 3,045,198; 4,224,595; and 4,237,721 all of which are by J. P. Dolan, individually or with others.

While an Adsistor detection device is currently contemplated, it is understood that other types of detection devices may be developed in the future which will not necessarily rely upon the variable resistance of the device but which could depend upon other parameters.

As shown in FIG. 1, the detection device 116 is mounted in a suitable fashion in a sensor housing 117 which is open at the bottom end thereof. The sensor housing 117 is joined to the pipe 115. The sensor 116 is connected to a pair of conductors or wires 118 which pass through the pipe 115 and out through the cap 102 of the sensor unit. In a preferred embodiment, the wires 115 are wrapped or otherwise mounted on the tether wire 113 and, ultimately, connected to a suitable electronic monitoring system (not shown in FIG. 1) which are referred to as a control panel or the like.

Referring now to FIG. 2, there is shown a bottom view of the sensor float 100 shown in FIG. 1. In this instance, there are shown six wedge-shaped compartments 104, 105, 106, 107, 108 and 109, respectively. The compartments 104 through 109 are arranged to incorporate therebetween appropriate channels such as channel 110 (see FIG. 1) as well as channels 201 and 202. These channels pass between the compartments and under the disk 103 to thereby permit water flow therethrough. The sensor 116 is shown mounted in the sleeve 117 as better shown in FIG. 1.

As noted above, the preferred embodiment includes the six wedge or pie shaped compartments. However, any other number can be provided, if desired. In addition to providing bouyancy, the wedge or pie-shaped configuration of the compartments also permits the sensor float 100 to be rotated as a result of water flow adjacent thereto.

By permitting the sensor float 100 to rotate in a relatively unconstrained fashion, a certain amount of agitation of the water flow through or under the sensor float 100 will occur. This agitation is helpful and advantageous in causing any effluent or hazardous waste in the water to be agitated and, thus, give off fumes more readily. These fumes are used to detect the presence of the hydrocarbons or other waste materials. With the agitation, as noted, the material detection can take place in a shorter time and with a smaller contamination factor (in the effluent) than would be possible without the agitation.

Clearly, the agitation aspect and the pie-shaped wedges 104 through 109 are not absolutely essential to the product and/or process but provide enhanced, preferable embodiments.

Moreover, it is possible to use a different number of wedges or to use a separate agitating mechanism such as a propeller, a mixer or the like. Also, the wedges can be replaced by vanes, ribs or the like. The ribs and/or vanes can be planar, arcuate, or the like, as may be determined by a particular application of the device.

In addition to the agitation which is created by the water passing through the various passages between the compartments, it is contemplated that bridging devices 175 can be connected between the narrow ends of the wedges or compartments. These bridges or spanning devices 175 can act as paddles in the water disposed beneath the vadous zone which is created in the housing 101. When the float 100 rotates as a result of the action of the water flowing thereby, these paddles will serve to further agitate the water under the vadous zone to enhance the admission of fluids and fumes in the vadous zone for detection by the sensor 116. Of course, the spanning or bridging devices 175 are not required in the invention.

Referring now concurrently to FIGS. 3 and 4, there is shown a schematic representation of a typical drainage channel and appropriate construction therein to enhance the operation of the instant invention.

The channel 300 is, typically, a conduit which is formed of concrete or other similar materials. Typically, these conduits are underground although this in not necessarily the case. In the embodiments shown in FIGS. 3 and 4, the conduit is substantially rectilinear unit although other shapes are contemplated. In any event, the conduit includes a floor 301, a ceiling 302 and side walls 303 and 304. This is a representative structure of a typical underground storm drain. The sensor flat 100 is shown tethered to the ceiling 302 of the storm drain 300. While not shown in FIG. 3, it is understood that the wires 118 can pass through the ceiling 302 to a suitable utility device.

Disposed on the floor 301 of the conduit 300, intermediate the sidewalls 303 and 304, is a chute or flume 400. This chute 400 or float control channel is, typically, centered with respect to the channel of the storm drain 300. The float control channel 400 comprises a pair of sidewalls 401 and 402 which are essentially parallel to each other as well as end wall 403 which is transverse to the side walls. A ramp or sloped interior wall 404 is provided adjacent to end wall 403 in such a fashion as to provide a slope from the floor of the drain conduit 300 to the top of the end wall 403. The ramp 404 is used to permit self-cleaning of the chute 400. That is, the chute 400 is, in a typical example, approximately one and one half feet high as measured from the floor 301 of the storm drain conduit. Thus, even with a relatively small water flow through the storm drain, the water can be effectively collected in the chute until it reaches the height thereof so that the sensor float 100 can float on the surface of the water. The water will spill over the end wall of 403 as indicated by the water flow 406. With relatively small to moderate waterflow, a continuing flow of water will be established through the chute 400. This flow will be sufficient to prevent the water in the chute 400 from becoming stagnant. Consequently, the condition of the water relative to the hydrocarbon waste is readily measured. Moreover, the waterflow will permit the agitation of these sensor floats as noted above.

However, when a relatively large or turbulent water flow exists in the drainage channel, the water will flow through chute 400 in such a fashion as to wash away any sediment or debris which has collected in chute 400. The debris is washed up and over the end wall 403 via ramp or slope 404. Of course, if the flow through the drainage channel is of extremely high volume so as to fill or substantially fill the drainage conduit, all portions of the channel will be cleansed in addition to the portion comprising chute 400.

Likewise, additional containment walls 407 and 408 can be constructed upstream from the end of the chute 400. These containment walls are, in the preferred embodiment, angulated relative to chute 400 so as to contain the water in the drainage channel and to cause the water to converge into the chute 400. In addition, sloped portions 409 and 410 are included upstream from the containment walls 407 and 408, respectively. These slopes or ramps are designed to be higher adjacent to the containment walls 407 and 408 than at the upstream portions of the drainage channel. Once again, the slopes 409 and 410 function as self-cleaning arrangements for the containment walls.

With a relatively slight trickle or flow of water through the drainage channel, water is "funneled" into the chute 400 as noted above. Again, with a relatively large water flow, some of the water will run up the ramps 409 and 410 and spill over the container walls 407 and 408, respectively. This operation will, in essence, cleanse that portion of the drainage channel, as well.

It is anticipated that the chute and containment walls within the drainage channel will be fabricated of concrete or other similar material. It is also contemplated that these containment walls and slopes will be formed permanently within the drainage channel.

However, it is within the contemplation of this invention that the chute 400 and the respective containment walls can be fabricated of metal, plastic, or some other material which is relatively inert and/or impervious to water and the toxic materials in question. In this case, the chute 400 and the associate containment walls can be detachably mounted in the drainage channel. The attachment can be made by means of bolts, rivets or any other suitable fasteners. Of course, a suitable adhesive such as epoxy or the like can also be used. Whether the internal "baffling and flow directing structures" (comprising chute 400 and the appropriate containment structure such as walls 407 and 408) can be constructed in place or consturcted in a remote location and transported to the sight for installation is at least partially a question of design.

Of course, it is also possible that the containment configuration can be built into the drainage system when it is initially constructed. Likewise, in the event of drainage channel systems which are fabricated of modular pipes (or tubes), the containment structure shown and described relative to FIGS. 3 and 4 can be incorporated into more and more modules which are inserted into the pipeline.

Likewise, in some instances, depending upon the configuration of the drainage system, the containment structure can be fabricated to one side or the other of the drainage channel. The centrally located containment apparatus including chute 400 is suggested as the preferred arrangement based upon existing drainage system construction. However, other construction techniques may warrant different arrangements.

Referring now to FIG. 5, there is shown a schematic side view of an extensive drainage system using multiple sensor floats and containment units. In this embodiment, an elongated drainage channel is shown. It is contemplated that this drainage channel may represent as much as several miles of drainage channel and is, therefore, not shown to scale. The drainage channel includes a ceiling 503 and a floor 504 similar to those shown and described above. In addition, a plurality of sensor float mechanisms 500 are suspended from the ceiling 503 by the appropriate tether line 513. Each of these sensor systems is contemplated to be substantially identical although modification between sensor systems is contemplated. The sensor system includes the vadous zone cylinder 501 which is equivalent to the cylinder 101 shown in FIG. 1. A separate containment structure 505 is associated with each of the sensor floats 500. A containment structure 505 is similar to a containment structure shown and described relative to FIGS. 3 and 4. These include the chute 400 and the containment walls 407 and 408 (see FIG. 4).

Also shown in FIG. 5 is a through-the-ceiling connection 510. This connection can include the means for attaching the tether 513 to the ceiling 503 and, as well, a suitable through-the-ceiling-conduit for passing the wires 118 shown in FIG. 1. The specific conduit or through-hole arrangement is not shown in specific detail. However, a via of any conventional configuration can be arranged. In addition, a separate connection box 511 is associated with each of the connector systems 510. The connector box can be mounted above the ground; it can be vault buried in the ground; it can be mounted directly to the outer surface of ceiling 503 of the drain channel; or the like.

In essence, the connector box 511 contains an electrical monitoring system which receives signals from the sensor 116 (see FIG. 1) in the sensor float 500. A suitable sensor box or monitoring circuit is of the type which is made by Spearhead Technology, Inc. of Seattle, Wash. Of course, other monitoring systems can be utilized, as well. The monitoring systems 511 are all connected, in this instance, to a master panel 512 which can be located at any suitable control location. The master panel 512 can provide any suitable indicia of activity of any one or more of the monitor panels 511.

Depending upon suitable plans or programs, a master panel can indicate that one or more monior circuits 511 have detected a toxic condition in the drainage channel. With a single, low level sensing, an "observation mode" can be achieved. In the event that a specified number of monitors 511, for example three or more, unsafe indications are received, the master panel can be arranged to provide a further alarm signal.

It is contemplated in accordance with one embodiment of this invention that when a specified unsafe condition is presented at the master panel 512, a signal is supplied to an activator 514. The activator 514 can be a suitable device such as a motor or the like. In this instance, the motor 514 is rendered operative as a result of signal from master panel 512 which causes gate 515 to swing closed in order to block the outlet of the drainage channel to thereby prevent the escape of the toxic or nauseous materials into the discharge area such as the ocean, a lake, a river or the like. The precise method and apparatus for causing the gate to swing closed is not part of this invention, per se. However, the gate can swing about the upper end thereof as indicated by hinge 516. Conversely, the gate can swing around a hinge (not shown) at one side of the gate. Of course, the gate can be fitted in slots or grooves so that it will move vertically or horizontally relative to the drainage channel.

Figure 6:
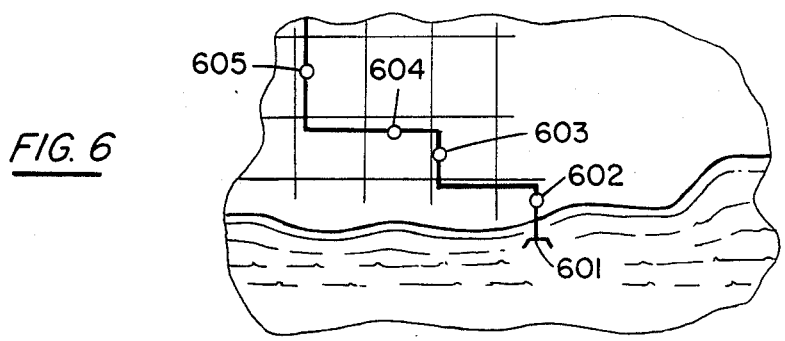
FIG. 6 is a schematic representation of a map or plat plan for a community with a drainage channel system superimposed thereon.

Referring now to FIG. 6, there as shown in schematic representation of an area map of a community or the like. The horizontal and vertical lines represent a grid of a particular (but hypothetical) community. These grid lines may represent streets in the community. The heavy line is representative of a storm drain system in the hypothetical community. The outlet of the drain system is indicated by outlet 601. Sensor locations are indicated by the circles 602, 603, 604 and 605. Of course, fewer or more sensors can be incorporated into any particular drainage system. Each of these sensors is considered to be equivalent to the sensor 500 and the monitor circuit 511 as shown in FIG. 5. Each of these sensors can be connected to a master panel (not shown in FIG. 6) akin to master panel 512 (see FIG. 5). Upon receipt of the appropriate number of signals from the sensors 602 through 605, the gate mechanism 515 (see FIG. 5) can be activated. In the alternative, if a gate is not used, the signal can alert the appropriate engineering personnel or the like in the community that a dangerous condition exists and that an appropriate action should be taken. For example, the gate mechanism can be closed or the system can be flooded with large amount of water whereupon a clean up operation can be initiated or any other action taken.

Figure 7:
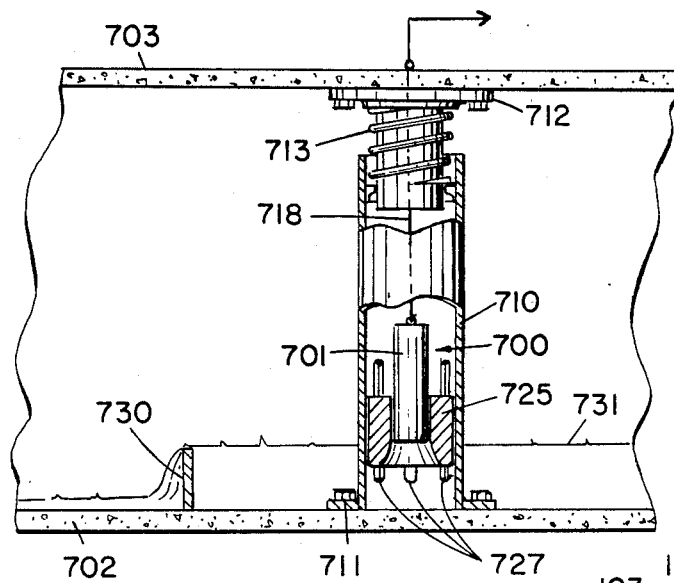
FIG. 7 is a partially broken away, schematic representation of an alternative embodiment of the instant invention.

Referring now to FIG. 7, there as shown a further embodiment of the instant invention. In this instance, a drainage channel having a floor 702 and a ceiling 703 is depicted. A sensor 700 is mounted within a hollow housing 710. Typically, the housing is cylindrical in shape and is secured in the drainage channel by means of inserting the bottom portion of the cylinder 710 into a collar 711 which is affixed to the bottom of 702 of the drainage channel. The top of the cylinder 710 is mounted in a collar 712 which is mounted at the ceiling 703 of the drainage channel. The upper portion of the cylinder 710 may include a telescoping member 713 which is, effectively, spring loaded or threadedly adjustable in order to permit the cylinder to be inserted between the collars 711 and 712. Of course, other suitable construction techniques can be used.

The sensor 700 includes the vadous zone cylinder 701 in which is mounted the sensor similar to sensor 116 in FIG. 1. The connectors 718 are connected to the sensor and passed outwardly from the system to the panels as suggested. A floatation device 725 is arranged to be attached to the lower portion of the vadous cylinder 701. The floatation device 725 is configured to support the cylinder 701 and to substantially conform to the inner configuration of housing 710. However, the floatation device 725 is adapted to move fairly readily within cylinder 710. A plurality of perforations which can be in the form of holes or slots 727 are provided through the cylinder 710, primarily adjacent to the lower or bottom portion thereof. These perforations permit water and effluent from the storm drain to enter into cylinder 710.

A weir 730 is formed across the width of the drainage channel, downstream from the cylinder 710 in order to provide a body of water as described relative to the FIG. 3. While it is not shown, a suitable ramp or slope can be incorporated adjacent to weir 730 in order to provide the self cleaning apparatus as described above.

In this embodiment, the cylinder 710 is put in place with the sensor mechanism 700 inserted therein and the wires 718 connected to monitor panels or master panels, as desired. As the water passes through drain system, it enters the cylinder 710 through the perforations 727. The float 725 causes the sensor to float on the surface of the water. The configuration of sensor 725, in conjunction with the vadous cylinder 701 operates to produce the vadous zone, as noted above. The appropriate fumes, fluids, or the like are created in the vadous zone whereupon they are sensed by the sensor element in the sensor device 700.

In the embodiment of FIG. 7, a tether is not essential, per se. Of course, a tether can be used, if so desired. One advantage of the device shown in FIG. 7 is that the containment device shown in FIGS. 3 and 4 is not essential, although the unit in FIG. 7 will operate properly with the aforesaid containment apparatus.

A disadvantage of the device shown in FIG. 7 is that a large flood of water or an unexpected amount of debris in the storm drain could adversely impact this arrangement. That is, the cylinder 710 can be broken and carried away (along with the remainder of the sensing system) or could act as a blockage in the system whereupon a damming effect could occur.

In the embodiments suggested in FIGS. 1 through 5, the sensor float would merely ride on the water flow and would tend not to act as a block in the system. Of course, with an inordinate water flow, the sensor shown in FIGS. 1 through 5 could be detached from the tether and washed out to sea or the like. However, inasmuch as the system floats, it could be recaptured and replaced.

Figure 8:
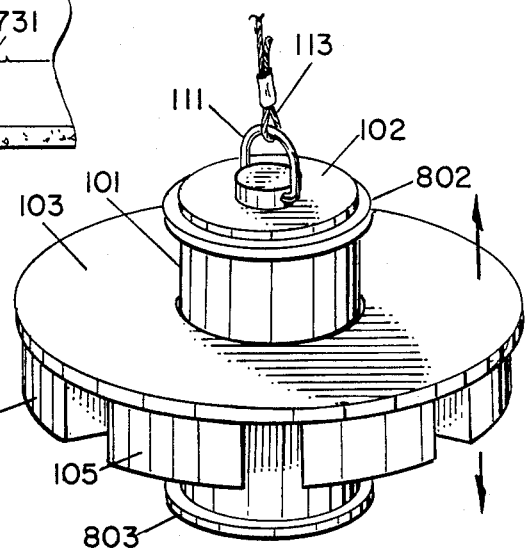
FIG. 8 is a schematic representation of an alternative construction of the sensor element container.

Referring now to FIG. 8, there is shown another embodiment of the instant invention. In this embodiment, the housing 101 is fabricated substantially as described relative to FIG. 1. That is, the bottom end remains open while the top end is closed by cap 102. The tether ring 111, sensor element 116 and so forth are mounted as before.

However, in this embodiment, an upper flange 802 is formed at the upper portion of housing 101. In similar fashion, a lower flange 803 is formed at the lower portion of the housing 101. The flanges can be located at the upper and lower extremities of the housing or at a distance therefrom.

In this arrangement, the disk 103 is arranged to be slideably or movably mounted on housing 101. Thus, the disk 103 can rotate, around housing and, as well, it can slip upwardly or downwardly in an axial direction relative to housing 101. However, the flanges 802 and 803 are arranged to prevent the disk 103 from passing thereover. In other words, the disk can move upwardly, downwardly and around the housing but it is captured between the flanges. This arrangement permits the sensor float to operate as described supra but permits the disk portion to rotate freely without twisting the tether lines and wires.

Thus, there is shown and described a unique monitoring system for detecting abnoxious, toxic or other undesirable materials in water flow, especially in storm drains. Preferred types of sensor floats are shown and described. However, those skilled in the art may conceive of modifications to the systems shown and described.

Moreover, those skilled in the art may develop other and, perhaps, more sophisticated sensing systems above ground for more sophisticated monitoring. However, any such modifications which fall within the purview of this description are intended to be included therein as well. That is, this description is intended to be illustrative only and is not intended to be limitative. Rather, the scope of the invention is limited only by the claims appended hereto.

We claim:

1. A monitoring system comprising,
sensor means for detecting a contaminant in a fluid, and
float means for supporting said sensor means adjacent the surface of said fluid,
said float means includes a plurality of bouyant segments which are spaced apart from each other to permit fluid flow therebetween.

2. The system recited in claim 1 wherein,
said sensor means includes a sensor device comprising an electrical element sensitive to exposure to liquids, vapors, or gases and operative to indicate the presence thereof.

3. The system recited in claim 2 wherein,
said sensor means includes a container for creating a vadous zone.

4. The system recited in claim 3 wherein,
said electrical element is mounted within the vadous zone created by said container.

5. The system recited in claim 3 wherein,
said container is supported by said float means.

6. The system recited in claim 5 wherein,
said container is attached to said float means.

7. The system recited in claim 5 wherein,
said container is rotatably and slidably mounted relative to said float means.

8. The system recited in claim 3 wherein,
said container is open at the bottom.

9. The system recited in claim 3 wherein,
said container comprises a hollow cylinder which is closed at one end.

10. The system recited in claim 2 wherein,
said electrical element is an adsorption type detection device.

11. The systen recited in claim 1 wherein,
said float meams includes at least one paddle means for agitating the fluid beneath said sensor means.

12. The system recited in claim 1 including,
control circuit means connected to receive signals from said sensor means when a contaminant is detected.

13. The system recited in claim 12 wherein,
said control circuit means includes alarm circuits for producing alarm signals which are used to produce a control function when a contaminant is detected in said fluid.

14. The system recited in claim 1 wherein,
said sensor means and said float means are disposed within a channel for carrying a fluid.

15. The system recited in claim 14 wherein,
said channel is a closed conduit for carrying water to a disposal location.

16. The system recited in claim 15 wherein,
said sensor means and said float means are tethered to an upper surface of said closed conduit.

17. The system recited in claim 15 including,
housing means mounted in said closed conduit and operative to maintain,
said sensor means and said float means disposed within said housing means.

18. The system recited in claim 17 wherein,
said housing means is mounted vertically in said closed conduit.

19. The system recited in claim 18 wherein,
said housing means includes at least one aperture therein so that fluid can enter into said housing.

20. The system recited in claim 17 wherein,
said housing means is adjustable in length.

21. The system recited in claim 14 wherein,
said channel comprises a drainage channel and said fluid comprises storm drain effluent.

22. The system recited in claim 1 including,
flow control means for controlling the flow direction of said fluid in the vicinity of said sensor means and said float means.

23. The system recited in claim 22 wherein,
said flow control means includes at least a weir disposed downstream from said sensor means and said float means in order to contain said fluid means in the vicinity thereof.

24. The system recited in claim 23 including,
at least one ramp means adjacent to said weir means whereby sediment in said flow control means can be selectively flushed over said weir means via said ramp means when a suitable fluid flow is provided.

25. The system recited in claim 22 wherein,
said flow control means includes closure means for blocking the flow of said fluid.

26. The system recited in claim 1 wherein,
said sensor device is suspended above the surface of said fluid by said float means.

27. The system recited in claim 1 wherein,
each of said plurality of bouyant segments are wedge-shaped.

* * * * *